United States Patent [19]

Orzales

[11] 4,113,960

[45] Sep. 12, 1978

[54] 3-(4'-ALKOXY-BENZOYL)-1,2,2-TRIMETHYL-CYCLOPENTANE-CARBOXYLIC ACIDS, THEIR OPTICAL ISOMERS AND DRUGS CONTAINING SUCH COMPOUNDS

[75] Inventor: Henri-Ange Orzales, Montpellier, France

[73] Assignee: Societe Civile de Recherches et d'Etudes Nouvelles, Paris, France

[21] Appl. No.: 705,535

[22] Filed: Jul. 15, 1976

Related U.S. Application Data

[63] Continuation-in-part of Ser. No. 540,504, Jan. 13, 1975, Pat. No. 4,025,552.

[30] Foreign Application Priority Data

Jul. 17, 1975 [FR] France .................. 75 22447

[51] Int. Cl.$^2$ .............................................. C07C 69/76
[52] U.S. Cl. ..................................... 560/52; 424/308; 424/317; 562/460
[58] Field of Search ...................... 260/473 R, 520 E; 424/308, 317

[56] References Cited

PUBLICATIONS

Bernstein, D.; Chem. Ber. 99(5) 1742–1745 (1966).

*Primary Examiner*—Paul J. Killos
*Attorney, Agent, or Firm*—Larson, Taylor and Hinds

[57] ABSTRACT

The invention relates to alkoxy-benzoyl-cyclopentanecarboxylic acids, and to their optical isomers; they are useful as active principles for anorexigenic drugs.

13 Claims, No Drawings

3-(4'-ALKOXY-BENZOYL)-1,2,2-TRIMETHYL-CYCLOPENTANE-CARBOXYLIC ACIDS, THEIR OPTICAL ISOMERS AND DRUGS CONTAINING SUCH COMPOUNDS

This application is a continuation-in-part of application Ser. No. 540,504, filed Jan. 13, 1975.

The invention relates to new compounds, having inter alia anorexigenic properties, a method of preparation thereof and drugs containing such compounds.

The compounds according to the invention are alkoxy-benzoylcyclopentanecarboxylic acids having the formula I

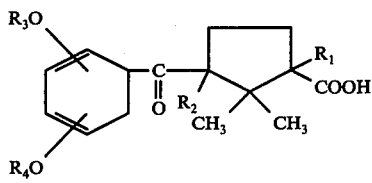

in which:

$R_1$ denotes a methyl or ethyl radical and $R_2$ denotes a hydrogen atom, or $R_1$ denotes a hydrogen atom and $R_2$ denotes a methyl or ethyl radical; and $R_3$ and $R_4$ both denote a lower alkyl radical or a hydrogen atom, or one of $R_3$ or $R_4$ denotes an ethyl group and the other one denotes a hydrogen atom.

The invention also relates to compositions containing a mixture of products having the formula I.

The invention also relates to racemic compounds, optically active isomers, and derivatives, inter alia physiologically acceptable esters and salts.

A group of compounds of the invention has the formula

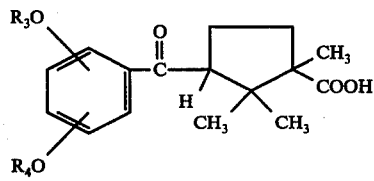

in which the substituents $R_3$ and $R_4$ have the meanings given previously.

Particular preference is given to : 3-(4'-ethoxy-benzoyl)-1,2,2-trimethyl-cyclopentane-carboxylic acid, and 3-(3',4'-dimethoxy-benzoyl)-1,2,2-trimethyl-cyclopentane-carboxylic acid.

Another preferred group of products according to the invention has the formula III

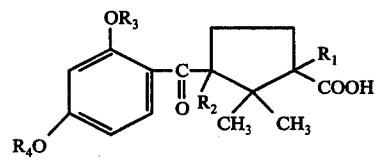

in which the substituents $R_1$ to $R_4$ have the meanings given previously.

Preference is given to compositions containing position isomers, i.e. products in which $R_1$ is a methyl or ethyl radical and $R_2$ is a hydrogen atom and products in which $R_1$ is a hydrogen atom and $R_2$ is methyl or ethyl radical. In a group of compositions according to the invention, the second type of isomers predominates and is present inter alia in the proportion of approximately 51 to 70% by weight of the mixture.

Particular preference is given to products according to the invention in which $R_3$ and $R_4$ both denote lower alkyl radicals. When the substituents $R_1$, $R_2$, $R_3$ or $R_4$ denote an alkyl radical, it is particularly advantageous for the latter to be a methyl radical.

According to the invention, the aforementioned products are prepared by a Friedel-Crafts or similar condensation reaction.

To this end, a substituted benzene derivative having the formula IV

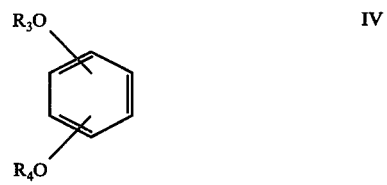

is reacted in the presence of a catalyst such as aluminum chloride, aluminum bromide or zinc oxide and, if need be, in the form of a solution in an organic solvent, with a camphoric anhydride having the formula V

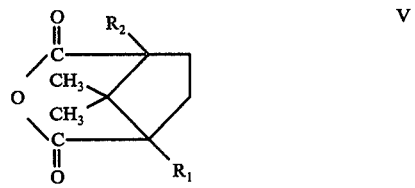

In these formulae, the substituents $R_1$ to $R_4$ have the meanings given previously.

Advantageously, the alkoxy-benzene and the camphoric anhydrid are added in the form of a mixture to the catalyst, or conversely.

Where a solvent is used the condensation step is performed in a solvent in which the starting reagents are soluble, advantageously at a temperature between $-5°$ and $+5°$ C, preferably approximately $0°$ C.

The products according to the invention can be isolated from the reaction medium by extraction with an aromatic solvent such as ether, which is subsequently eliminated by distillation. The optical isomers of the compounds according to the invention are obtained, in the above process, when starting from the corresponding optical isomers of the camphoric anhydrid.

According to the invention, it is possible to obtain any one of the position isomers or a mixture of isomers within a desired range of proportions, by varying the polarity of the solvent used.

Thus, by using a highly polar solvent, one can obtain isomers in which $R_1$ is a methyl or ethyl radical.

If the solvents used have progressively lower polarity, the mixture will be correspondingly richer in isomers in which $R_2$ denotes a methyl or ethyl radical.

The high-polarity solvents may with particular advantage be substances such as nitromethane. The lower-polarity solvents yielding a mixture of isomers including a predominant proportion of those of the second type may with particular advantage be solvents such as carbon disulphide and 1,2-dichloroethane.

The position isomers can each be isolated from the mixture by conventional methods of separation such as crystallization or distillation. Alternatively, the mixture of acids can be treated with an alcohol to form the corresponding esters and the latter can be subjected e.g. to fractional crystallizations. The thus-separated esters are then saponified to obtain the corresponding acids.

To illustrate the invention we now give examples of the preparation of cyclopentane carboxylic acids.

EXAMPLE 1

The preparation of the levorotatory 3-(4'methoxy benzoyl)-1,2,2-trimethyl-cyclopentane-carboxylic acid (compound 1) of the formula VI

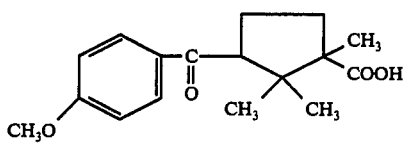

VI 10 gr. (0.055 mole) of 1-camphoric anhydrid $(\alpha_D^{20°\,C} = 3.2°)$ are dissolved under stirring in 162 gr. (1.5 mole) of methoxy-benzene. 14.6 gr. (0.11 mole) of aluminum chloride are added portionwise, at ambient temperature and under stirring, to the above solution. After 2 hours of stirring, the reaction mixture is decomposed by ice and a 10 % solution of sulphuric acid. The mixture is extracted with ether (in toto 350 ml) and the total ether solution recovered is washed with water. The ether solution is thereafter treated with 100 ml of a 2 % aqueous solution of sodium hydroxyde. The alcaline solution obtained is acidified at pH3 with an acid solution, in the present case hydrochloric acid. The crude compound which is isolated is crystallized in benzene. 10 gr. of the above identified isomer are obtained in the form of white crystals. The physical constants of the products according to the invention are as follows :
M P = 176° C
$[\alpha]_D^{20°\,C} = 20°,2$ ( $l = 1$ ; $c = 3$, chloroform) main bands in infra-red in cm$^{-1}$ (KBr pellet) : 2960, 1690, 1650, 1590, 1235, 1170, 840, 600.

EXAMPLE 2

Preparation of the dextrorotatory 3-(4'-methoxy benzoyl)-1,2,2-trimethyl-cyclopentane-carboxylic acid (compound 2) of the formula VI given previously The reaction is carried out substantially as in example 1, starting however from the dextrorotatory isomer of camphoric anhydrid. 10 gr. of the compound are obtained in the form of white crystals which, after crystallisation in benzene, have a melting point of 165°-166° C.

EXAMPLE 3

Preparation of the racemic compound of 3-(4'-methoxy-benzoyl)-1,2,2-trimethyl-cyclopentane-carboxylic acid (compound 3) of the formula VI given previously.

In the same manner, the racemic compound is obtained starting from the racemic form of camphoric anhydrid. Its melting point is of 165°-166° C.

EXAMPLE 4

One prepares in the same manner, starting each time from the corresponding alkoxybenzene, the following compounds : 3-(4'-ethoxy-benzoyl)-1,2,2-trimethyl-cyclopentane-carboxylic acid : MP = 122° C (compound 4) of the formula VII

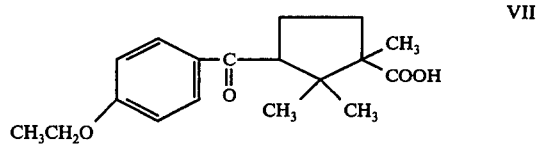

and 3-(3', 4'-dimethoxy-benzoyl)-1,2,2-trimethyl-cyclopentane-carboxylic acid : MP = 154° C (compound 5) of the formula VIII

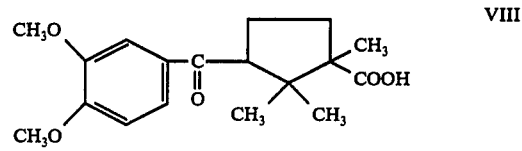

EXAMPLE 5

Preparation of a mixture of levo 3-(2', 4'-dimethoxybenzoyl) 2,2,3-trimethyl cyclopentane carboxylic acid and levo 3-(2',4'-dimethoxybenzoyl) 1,2,2-trimethyl cyclopentane carboxylic acid having the formula IX and X respectively (compounds 6 and 7).

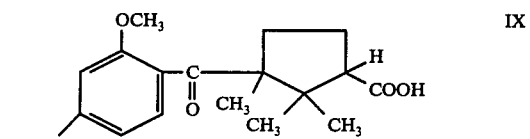

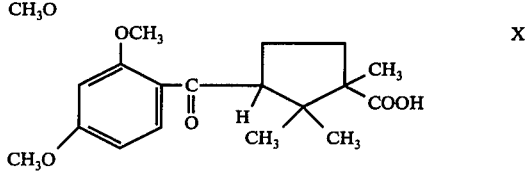

2.5 g. of D (+) camphoric anhydride was mixed with 2.7 g of 1,3-dimethoxybenzene in 30 ml of 1,2-dichloroethane. 3.8 g aluminum chloride was added in portions at 0° C with agitation. After the reaction medium had returned to ambient temperature, it was agitated for 2 more hours. The reaction medium was poured on to ice and hydrochloric acid was added, followed by extraction with ether.

After the etheral solution had been washed and the ether had been distilled, the yield was 3 g of an oil which slowly crystallized and consisted of a mixture of 47.5% 3-(2', 4'-dimethoxybenzoyl) 1,2,2-trimethyl cyclopentane carboxylic acid and 52.5% 3-(2',4'-dimethoxybenzoyl) 2,2,3-trimethyl cyclopentane carboxylic acid.

EXAMPLE 6

Preparation of levo 3-(2'-dimethoxybenzoyl) 2,2,3-trimethyl cyclopentane carboxylic acid having the formula IX given previously (compound 6). 500 ml of saturated anhydrous methyl alcohol (with dry hydrochloric acid gas) was added to 16 g of a mixture of acids similar to that obtained in Example 1, followed by refluxing for 4 minutes. After distillation of the alcohol, the yield was 11 g of a mixture of methyl esters corresponding to the aforementioned acids. The mixture of esters was recrystallized from petroleum ether, thus isolating 4.6 g of 3-(2',4'-dimethoxybenzoyl) 2,2,3-trimethyl cyclopentane carboxylic methyl ester, melting at 108° C.

The 2 g of ester was saponified with 30% alcoholic potash (2 hours' reflux), yielding 5.5 g 3-(2',4'-dimethoxy-benzoyl) 2,2,3-trimethyl cyclopentane carboxylic acid, melting at 134° C.

Determinations made on the acid yielded the following results:

|  | Microanalysis | |
|---|---|---|
|  | C % | H % |
| theoretical | 67.5 | 7.5 |
| found | 67.39 | 7.56 |

Rotatory power = $[\alpha]_D 20°$ C = $-14.1$ (1 = 1; c = 2.5) in $CH_3Cl$.

EXAMPLE 7

Preparation of racemic 3-(2',4'-dimethoxybenzoyl) 2,2,3-trimethyl cylcopentane carboxylic acid having the formula IX given previously (compound 8).

The method was the same as in Examples 5 and 6 except that levo camphoric anhydride was replaced by the corresponding racemic derivative. The yield was 4.6 g methyl ester melting at 82° C and 5.5 g racemic acid melting at 158° C.

EXAMPLE 8

Preparation of levo 3-(2',4'-dimethoxybenzoyl) 1,2,2-trimethyl cyclopentane carboxylic acid having the formula X given previously (compound 7). 2.5 g of levo camphoric anhydride was mixed with 2.7 g of 1,3-dimethoxybenzene in 30 ml nitromethane. 3.8 g aluminum chloride was added in portions at 0° C with agitation. After the reaction medium had returned to ambient temperature it was agitated for a further 2 hours. The reaction mixture was poured on to ice. Hydrochloric acid was added, followed by extraction with ether.

After the ethereal solution had been washed and the ether had been distilled off, a residue was obtained which, when crystallized from the mixture of ethanol and water of ether and petroleum ether, yielded 1.7 g 3-(2',4'-dimethoxy-benzoyl) 1,2,2-trimethyl cyclopentane carboxylic acid melting at 145° C.

Determinations made on this acid yielded the following results:

|  | Microanalysis | |
|---|---|---|
|  | % C | % H |
| Theoretical | 67.5 | 7.5 |
| Found | 67.35 | 7.55 |

Rotatory power: $[\alpha]_D 22°$ C = $-51.4°$ (c = 2.5; 1 = 1) in $CH_3Cl$.

EXAMPLE 9

Preparation of racemic 3-(2',4'-dimethoxybenzoyl) 1,2,2-trimethyl cyclopentane carboxylic acid having the formula X given previously (compound 9).

The method was the same as in Example 6, except that racemic camphoric anhydride was used. The yield was 1.7 g of acid melting at 182° C.

The invention also relates to drugs containing at least a compound of the formula XI

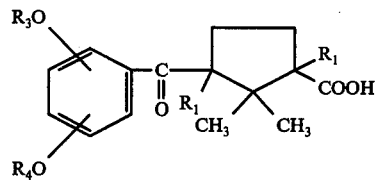

in which:

R₁ denotes a methyl or ethyl radical and R₂ denotes a hydrogen atom, or R₁ denotes a hydrogen atom and R₂ denotes a methyl or ethyl radical; R₃ and R₄ each denotes a lower alkyl group or a hydrogen atom, and the optical isomers thereof and/or derivatives, inter alia esters and salts of addition with physiologically tolerated acids. These compounds have specially noteworthy therapeutic properties, inter alia anorexigenic properties, which are all the more unexpected as they contain only carbon, hydrogen and oxygen, whereas, usually, the known anorexigenic properties, which are all the more unexpected as they contain only crbon, hydrogen and oxygen, whereas, usually, the known anorexigenic compounds also contain nitrogen in their molecule and are of the amphetamine type.

The anorexigenic properties of the drugs according to the invention are shown by the results of the pharmacological tests given hereinafter.

Tests were performed on dogs (female Beagle dogs) having an average weight of 10 kg. and which received 100 mg/kg. of compound 1. 30 minutes thereafter they were presented their usual food, but ate less than the third of the average amount of food eaten by controls. The above dose of compound was perfectly tolerated by the animals. It did not induce any substantial change in their general behaviour.

Similar tests were run on male rats of the Wistar type, having an average weight of 150 g. They were divided in groups (each of which comprised 10 animals) which were given orally the compounds 1, 2, 3, 4, and 5 respectively, in the form of a 1% solution of the tested compounds, at a dose of 1 ml/100 gr of body weight, during 5 days.

A reduction of the amount of food eaten was observed from the first day. A reduction of the body weight started on the third day.

In other tests, the effet of 3-(2',4'-dimethoxy-benzoyl) 1,2,2-trimethyl cyclopentane carboxylic acid and 3-(2',4'-dimethoxybenzoyl) 2,2,3-trimethyl cyclopentane carboxylic acid and a mixture of these acids as in Example 5 was observed on the amount of food ingested by rats. The method was as follows:

Male rats of the Wistar strain (average weight 150 g) were divided into batches of 10 animals. Each animal was placed in an individual cage. During the 2 days before the test, the amount of food consumed by the animals in 24 hours was determined by weighing. Next, the animals were treated as follows for 5 days:

9 a.m. : weighing
9 30 a.m. : oral administration of a 1% solution of the products according to the invention to the rats, in the proportion of 5 mg/kg rat, and of the same volume of distilled water to the control animals,
10 a.m. : calculation of the amount of food consumed in 24 hours by weighing the remaining food.

On the first day of treatment, a decrease was observed in the amount of food ingested by the treated rats. The body weight decreased from the second day of treatment.

At the end of the fifth day, the decrease in food intake was 52%, 48% and 53% respectively, compared with the control animals. The decrease in body weight was 15%, 12% and 16% respectively, compared with the control animals.

These results show the importance of the anorexigenic effect of the drugs according to the invention, particularly the effect of the mixture of position isomers in Example 5.

The products used in the drugs according to the invention are substantially devoid of toxicity. Their harmlessness is particularly noteworthy. The $LD_{50}$ in the mouse was determined by orally administering the derivatives in the form of an aqueous suspension in water. The results obtained with 3-(2',4'-dimethoxybenzoyl) 1,2,2,-trimethyl cyclopentane carboxylic acid and 3-(2',4'-dimethoxybenzoyl) 2,2,3-trimethyl cyclopentane carboxylic acid are 1.50 g/kg and above 5 g/kg respectively. The $LD_{50}$ obtained on mice, for compound 1, were as follows : orally : 5 gr/kg ; intraperitoneally : 500 mg/kg; intraveneously : 125 mg/kg.

Owing to their advantageous properties, the compounds of formula are valuable active principles inter alia for treating all types of obesity and excess weight. They can be used as such, or in the form of their physiologically acceptable salts.

The unit dose is about 20–100 mg, preferably 40 –75 mg, and the daily dose is approximately 100–300 mg preferably approximately 50–200 mg.

In the drugs according to the invention, the substances are preferably administered orally in the form of cachets, tablets, pills, dragees or solutions in ampules. In all cases they can be associated with inert media or excipients of the kind conventionally used for this galenic treatment.

Therefore, the invention also relates to the solid pharmaceutical compositions containing said compounds and to the drinkable solutions of said compounds.

Alternatively, the products can be rectally or parenterally administered.

The invention is also particularly concerned with the compositions containing the compounds according to the invention, in association with suppository carriers, as well as with the injectable solutions containing said compounds in association with an injectable sterile liquid.

Clearly, and as the preceding shows, the invention is in no way limited to those applications or embodiments described in detail, but includes all variants.

I claim:

1. Carboxylic acids, characterized in that they have the formula III

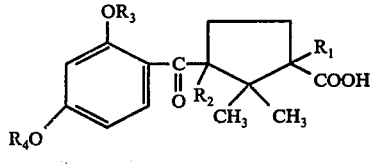

in which:

$R_1$ denotes a methyl or ethyl radical and $R_2$ denotes a hydrogen atom, or $R_1$ is a hydrogen atom and $R_2$ denotes a methyl or ethyl radical; and $R_3$ and $R_4$ denote a lower alkyl radical or a hydrogen atom, and the optical isomers and/or the alkyl esters and the salts of addition with physiologically tolerated acids.

2. Acids according to claim 1, characterized in that $R_3$ and $R_4$ both denote lower alkyl radicals.

3. A mixture according to claim 1 containing products having the formula III in which $R_1$ is a methyl or ethyl radical and $R_2$ is a hydrogen atom and products having the formula III in which $R_1$ is a hydrogen atom and $R_2$ is a methyl or ethyl radical, or their corresponding alkyl esters or salts.

4. A mixture according to claim 3 comprising of approximately 51 to 70% by weight, of products in which $R_1$ is a hydrogen atom and $R_2$ is a methyl or ethyl radical.

5. Racemic or levo carboxylic acids, characterized in that the substance in question is 3-(2'4'-dimethoxy benzoyl) 2,2,3-trimethyl cyclopentane carboxylic acid, 3-(2'4'-dimethoxy benzoyl) 1,2,2-trimethyl cyclopentane carboxylic acid or a mixture thereof.

6. The methyl esters of the acids according to claim 5.

7. A pharmaceutical composition comprising an anorexigenic amount of a compound having the formula III

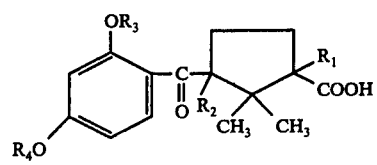

in which:

$R_1$ denotes a methyl or ethyl radical and $R_2$ denotes a hydrogen atom, or $R_1$ is a hydrogen atom and $R_2$ denotes a methyl or ethyl radical; and $R_3$ and $R_4$ denote a lower alkyl radical or a hydrogen atom, and the optical isomers and/or the alkyl esters and the salts of addition with physiologically acceptable carrier.

8. A pharmaceutical composition, according to claim 7, characterized in that it is administered in unit doses of 20 to 100 mg and in daily doses of 100 to 300 mg.

9. A method for inducing an anorexigenic condition in man or animal which comprises administering to said man or animal an anorexigenic amount of a compound of formula III according to claim 1.

10. A mixture of the racemic or levo carboxylic acids, according to claim 4 in the proportions of approximately 52.5% and 47.5% respectively by weight.

11. A pharmaceutical composition, according to claim 7, containing as active ingredient the racemic or levo 3-(2',4'-dimethyxy benzoyl) 2,2,3-trimethyl cyclopentane carboxylic acid.

12. A pharmaceutical composition, according to claim 7, containing as active ingredient the racemic or levo 3-(2',4'-dimethoxy benzoyl) 1,2,2-trimethyl cyclopentane carboxylic acid.

13. A pharmaceutical composition, according to claim 7, containing as active ingredient the racemic or levo 3-(2',4'-dimethoxy benzoyl) 2,2,3-trimethyl cyclopentane carboxylic acid, and the racemic or levo 3-(2',4'-dimethoxy benzoyl) 1,2,2-trimethyl cyclopentane carboxylic acid.